United States Patent [19]

Larribas

[11] 4,409,989
[45] Oct. 18, 1983

[54] URINE SPECIMEN CUP

[76] Inventor: Daniel Larribas, 9401 Stanfield Ct., Stockton, Calif. 95209

[21] Appl. No.: 302,299

[22] Filed: Sep. 14, 1981

[51] Int. Cl.³ .............................................. A61B 10/00
[52] U.S. Cl. ..................................... 128/760; 4/144.1; 4/661
[58] Field of Search .............. 128/760, 761, 294, 295, 128/272, 275; 4/144.1–144.4, 114.1, 451, 454, 457, 462, 661; 206/217, 219, 519, 520; 220/70; 604/329

[56] References Cited

U.S. PATENT DOCUMENTS

| 380,009 | 3/1888 | Wundt | 312/351 |
| 2,936,920 | 5/1960 | Wallace | 220/70 X |
| 3,407,922 | 10/1968 | Palmer | 206/217 |
| 3,602,923 | 9/1971 | Girala | 128/295 X |
| 3,629,873 | 12/1971 | Long | 4/144.2 X |
| 3,711,871 | 1/1973 | Sherin | 4/144.1 |
| 3,920,120 | 11/1975 | Shveda | 206/217 |

Primary Examiner—Kyle L. Howell
Assistant Examiner—Christine A. Fukushima
Attorney, Agent, or Firm—Mark C. Jacobs

[57] ABSTRACT

An improved urine specimen cup is disclosed which is anatomically convenient and which is adapted to receive a small towelette to dry the genital area.

14 Claims, 16 Drawing Figures

URINE SPECIMEN CUP

BACKGROUND OF THE INVENTION

In these days of greater awareness of the need to care for our bodies, more and more men and women are having routine physical examinations. As a part of these physicals a urine specimen is usually collected for analysis. These specimens are collected in what are designated as specimen cups.

Most prior art specimen cups are generally round in cross section with a flared top round portion slightly wider than the balance of the cylinder. Sometimes these are threaded to receive a closure thereon.

One problem associated with such cups is that they are not anatomically accomodating for either males or females. If one's accuracy is not good, the result will be a profusion of urine on the skin, clothing or the carpet.

Since most people utilize toilet paper when they urinate, it would be pleasing to them to have a readily available piece of toilet paper or suitable substitute when utilizing a specimen cup.

Thus the general object of this invention is to provide an improved urine specimen cup.

Another object is to provide an anatomically accommodating specimen cup.

Still another object is to provide an easily closable specimen cup which is easy to grasp.

Yet another object is to provide a specimen cup adapted to hold a piece of toilet paper or equivalent.

A further object is to provide a stackable specimen cup for easy storage and dispensing.

These and other objects and advantages of this invention will be made more apparent from the specification and the appended claims.

SUMMARY OF THE INVENTION

The invention herein comprises a novel stackable and dispensable specimen cup which has a generally oval cross sectional top portion tapering to and communicating with a generally oval or round middle and bottom sections of the specimen cup. The bottom section includes a recess adapted to receive a towelette or sheet of toilet paper. The top lip is curved outwardly and downwardly in a hemispherical configuration adapted to engage a snap cap configured to engage the top lip to sealingly close the specimen cup.

DESCRIPTION OF THE PREFERRED EMBODIMENT

Reference is now made to the drawings wherein two slightly different embodiments of the device of this invention are disclosed. In the first, the base portion is oval as per reference to FIG. 10, while in the second embodiment the base portion is round, as per FIG. 12. In each of these the cup 10, the outside wall 12 is one continuous member. Thus the cup could be readily made by injection moulding. For ease of understanding and distinction of the two embodiments, each will be described as having three sections, top, middle, and lower, which sections are of course contiguous and connected to each other.

Figure 1:
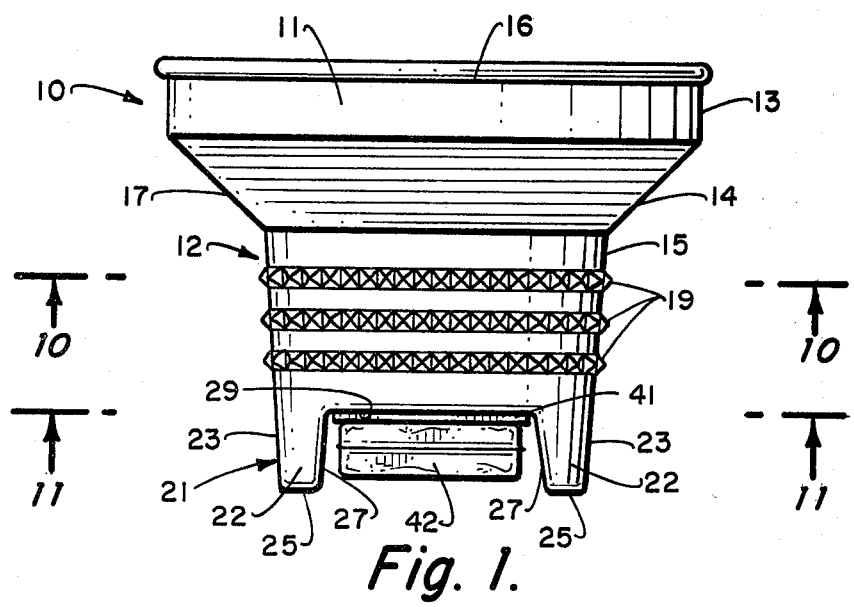
FIG. 1 is a front elevational view of a first embodiment of this invention.

Turning now to FIG. 1 there is seen a urine specimen cup 10 having a top body portion 11 which has a top lip 16 that curves arcuately outward in a hemisphere and which extends beyond the top portion downward, extending to upper side wall 13. Said wall 13 terminates at downwardly and inwardly extending lower side wall 14 which wall extends to the middle section of the body 15, which will be discussed below.

Figures 2, 3:
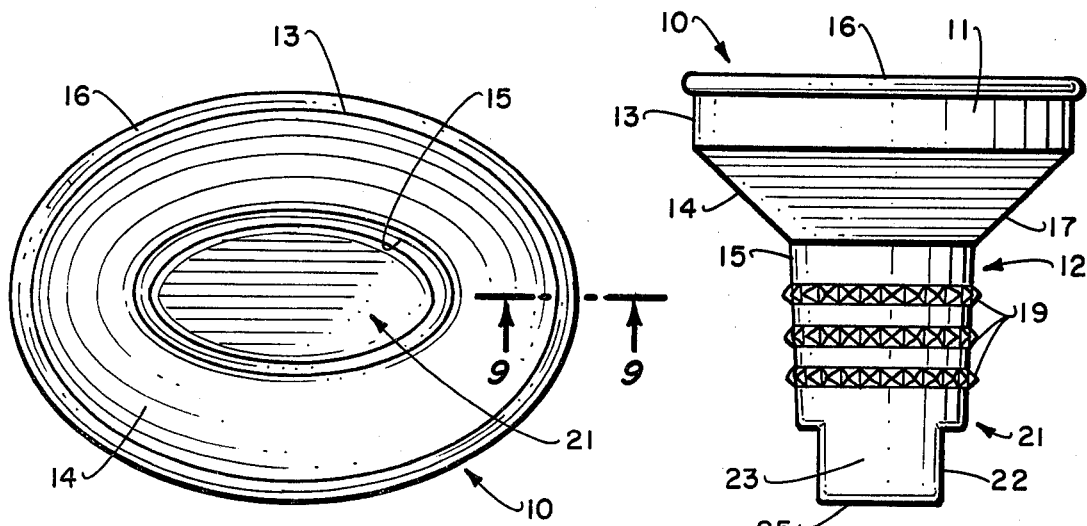
FIG. 2 is a top plan view of the first embodiment of the specimen cup of this invention.
FIG. 3 is a side elevational view of the device of FIG. 1.

As is seen from FIG. 2 the top portion 11 of the device 10 is oval. Typical dimensions including the small encircling lip 16 are 3.5 inches×2.5 inches.

The middle portion 15 hereof is also oval. This portion commences at the lower terminus of the top portion and comprises downwardly and slightly inwardly extending middle sidewall 17 which extends down to the lower portion to be discussed below. Overlaying the middle side wall 17's lower third are optional ridges 19 which are raised outwardly about 1/16th of an inch. Alternately these ridges instead of being stacked rings as shown, can comprise a raised hatched area. The purpose of the raised section 19 is to aid the user to grip the device of this invention. The ridged section also serves as a reinforcement for the side walls.

The bottom portion 21 hereof comprises two spaced apart arcuate sections co-extending downward from the end of the middle portion hereof. Said bottom portion includes the spaced apart legs 22 each of which is a mirror image of the other and each of which includes the outer wall 23 which extends downwardly and tapering inwardly slightly at the same angle as the side wall of the middle portion hereof.

Each leg further includes a flat bottom wall 25 and a generally upward extending inner wall 27 which may be vertical or angular as desired.

The space between the upper edges of the legs 22 comprises 29 the bottom wall of the middle portion hereof. The elevation of the legs 22 may be between about ½ and ¾ inches.

The underside of bottom wall 29 is adapted to optionally receive a state of the art adhesive strip 81, which prior to application includes the following layers:

a. release layer
 b. adhesive layer c. material such as a thin mylar © sheet
d. a second adhesive layer
e. a second release layer Such tapes having two adhesive sides are readily available in the marketplace, from such vendors as the 3M Company among others.

Said dual side adhesive tape is intended to secure a towelette,—a piece of paper towel—, of a sheet of toilet paper or other suitable wiping material. Such towelettes are a standard packaged article. These may comprise a small sheet of paper enclosed in foil pouch or merely a sheet of folded paper as may be desired. This towelette may be used to wipe one's body or the hand depending upon the dirtiness of the user.

Figure 4:
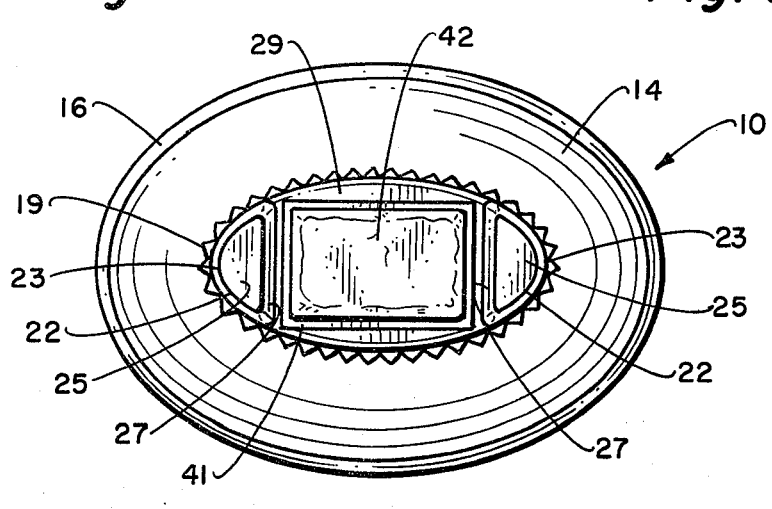
FIG. 4 is a bottom plan view of the device of FIG. 1.

Reference is made to FIG. 4 which illustrates the underside of the device of FIG. 1.

It is seen that the spaced legs 22 conform in their outer curvature to the device as it tapers downwardly in an oval shape.

The towelette which as indicated may be prepackaged in a sealed pouch 42 is shown adhered to 29 by adhesive 41 in FIG. 1.

FIG. 3, not previously described shows the current study of the legs 22 and specifically illustrates the outer wall 23 of the legs 22 as it blends in and continues from the termination of the central portion of the body 11. FIG. 3 is a side view of the device of FIG. 1 oriented 90 degrees horizontally.

Figure 10:
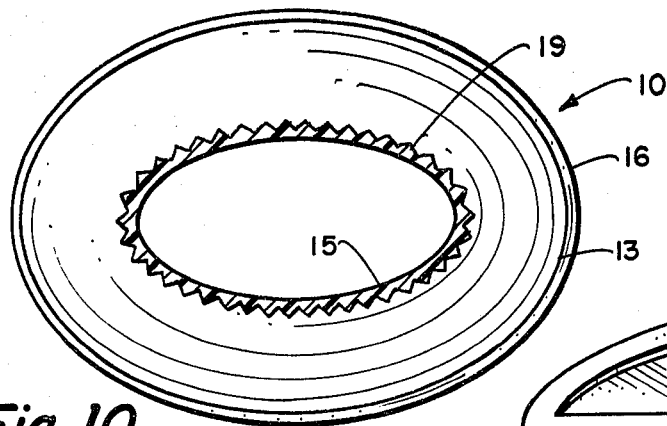
FIG. 10 is a cross section view taken along the line 10—10 of FIG. 1.
Figure 11:
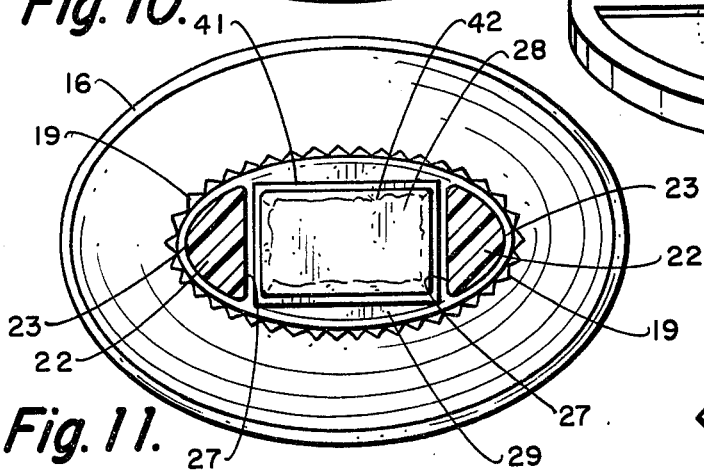
FIG. 11 is a cross section view taken along the line 11—11 of FIG. 1.

Skipping forward to FIGS. 10 and 11 which are sectional views along the lines 10—10 and 11—11 of FIG. 1 it is seen that these aid the reader to understand the generally oval shape of the middle and lower portion of the body of this first embodiment.

In FIG. 10, the ridges 19 are shown superimposed on the outer surface of the side wall 15. These serve the user by providing a readily grippable surface. While shown as ridges 19, this raised surface may be cross hatched or otherwise scored to provide a sure grip cup encircling surface.

FIG. 11 taken along line 11—11 of FIG. 1 illustrates the construction of the lower or bottom portion 21 being generally oval in shape. Lower outer wall 23 is seen to be arcuate and to connect on each end to intermediate wall 27. Per FIG. 1 as well, these two lower segments 22 each designated 21 are spaced apart by space 28. Space 28 is slightly wider than underwall 29 of the middle section, since the intermediate walls 27 are disposed divergently outward from the edge of underwall 29.

Turning now to the second embodiment of this improved specimen cup. Reference is made to FIGS. 5,6,7 and 8. As is seen the wall 54 corresponds to wall 14. This embodiment is to be described in three portions as was indicated previously of the three portions of cups 52 and 12 the top or upper portions are exactly same. Therefore the description of the top lip 16 is applicable to its counterpart 56, the balance of the structure of the upper portion 51 is the same in configuration as body top portion 11 in the earlier embodiment. First side 53 is seen to commence at the end of lip 56 and to depend downwardly to inwardly depending wall 54. From FIG. 6, the top plan view, it is seen that the top section is oval, but unlike its counterpart of FIG. 2 it tapers down to a circular mid and lower portions 55 and 61 respectively. Inner side wall 54 diverges to a point at which middle side wall 55 commences, this last mentioned depending generally vertically. Middle side wall 55 includes at its lower third circumscribing ridges 59.

Middle side wall 55 is contiguous with and of the same dimension as the outer wall 63 of lower portion 61. Here walls 55 and 63 are coplanar. Lower outer wall 63 extends to bottom wall 65 and forms a generally right angle thereto. Inner walls 67 also intersects bottom wall 65 at a right angle and taken together 63, 65 and 67 form foot 62. As is seen there are two of these spaced apart feet 62. The feet extend upwardly. The elevation of lower inner wall 67 which extends to a point where it intersects underwall 69. Underwall 69 is disposed at or slightly below the circumscribing ridge 59.

Figure 7:
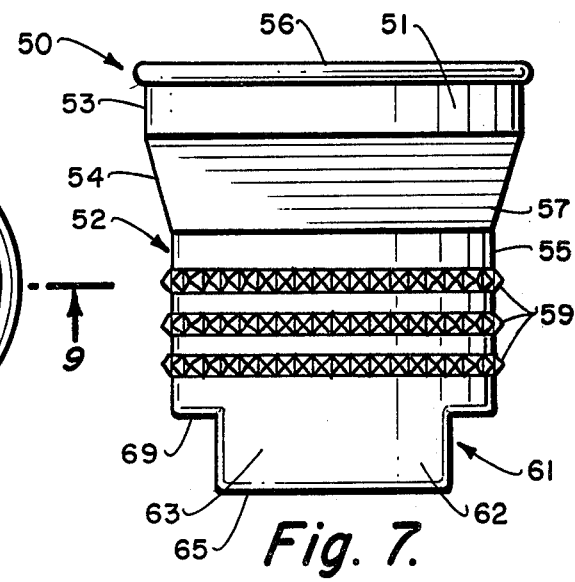
FIG. 7 is a side elevation of the device of FIG. 5.
Figure 8:
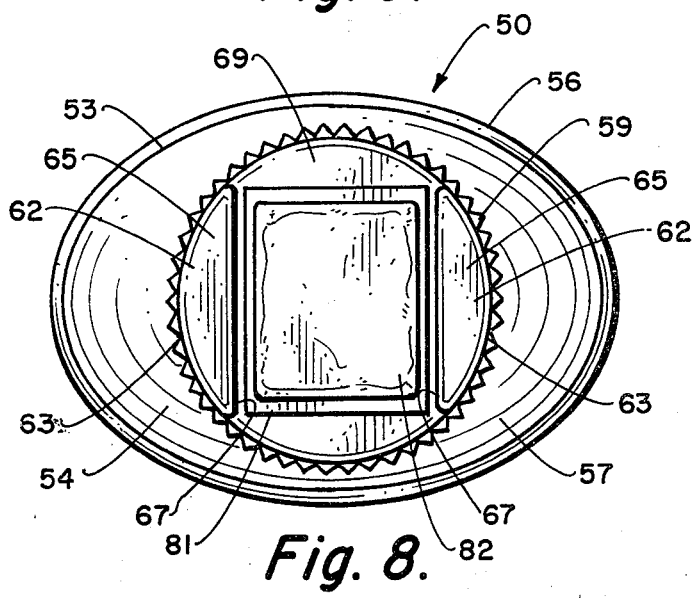
FIG. 8 is a bottom plan view of the device of FIG. 5.

FIG. 8, the underside view, illustrates the circular configuration of the lower portion 61. Here the 2 spaced apart legs 62 which are hemispherical are illustrated as being spaced apart. Their continuity with the center portion of the devices is seen from the orientation of the viewer as presented in FIG. 7.

FIG. 8 also illustrates the disposition of optional towelette or other wiping surface 82 to the underside of underwall 69.

Figure 5:
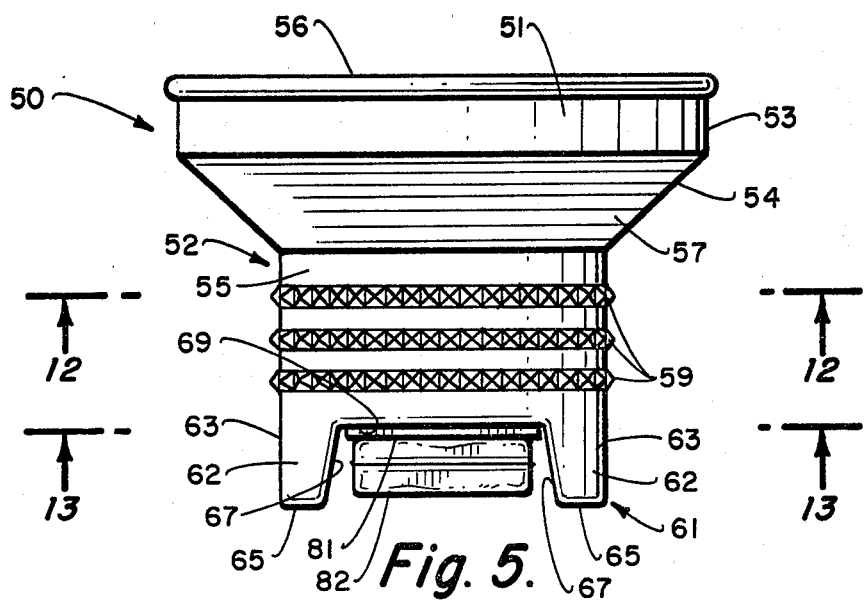
FIG. 5 is a front elevational view of a second embodiment hereof.
Figure 6:
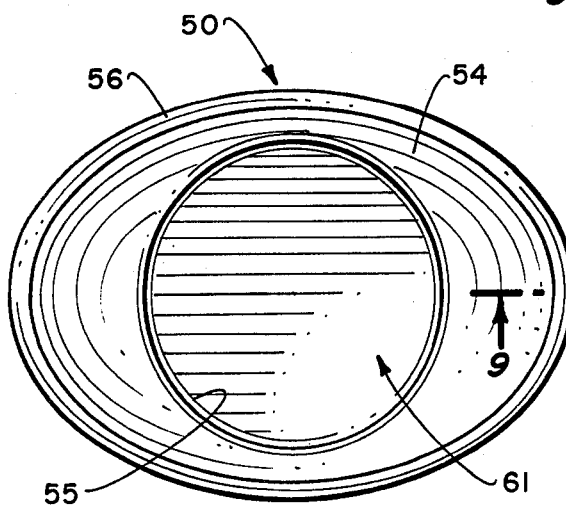
FIG. 6 is a top plan view of the device of FIG. 5.
Figure 12:
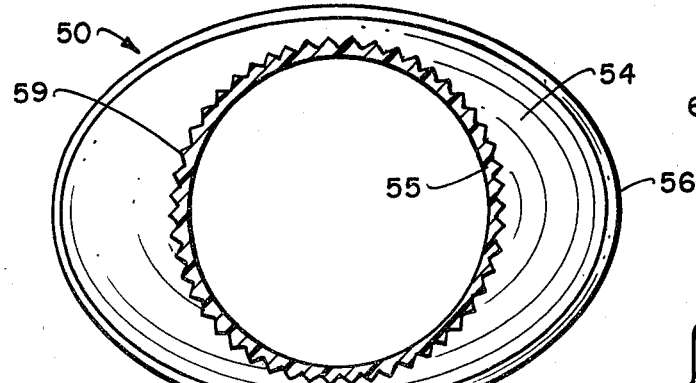
FIG. 12 is a cross section view taken along the line 12—12 of FIG. 5.

FIG. 12 is a sectional view taken along the line 12—12 at FIG. 5 just at ridges 59. These ridges have been previously discussed.

Figure 13:
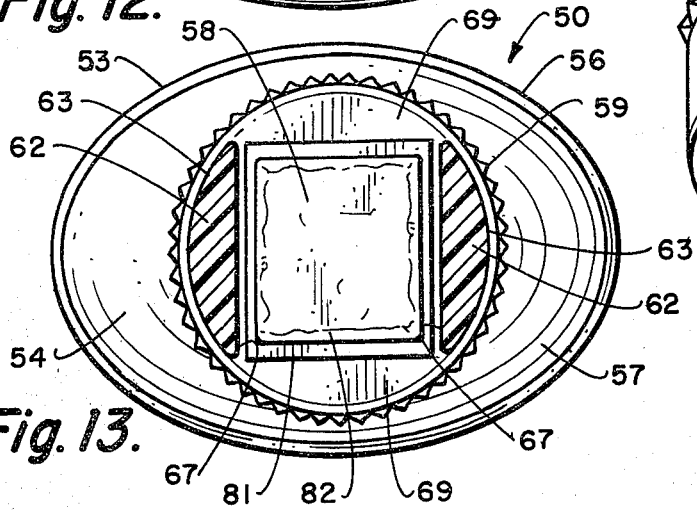
FIG. 13 is a cross section view taken along the line 13—13 of FIG. 5.

FIG. 13 is a sectional view taken along the line 13—13 of FIG. 5 illustrates the circular nature of the bottom portion of device 50. It is seen that legs 62 separated by space 58 form a circle as opposed to the oval of FIG. 11.

The reader's attention is returned briefly to the content of FIGS. 3 and 7 in that the configuration of the middle and lower portions in FIG. 3 is a continual decreasing oval while for FIG. 7 it is a constant sized circle, i.e., a cylinder.

Figure 9:
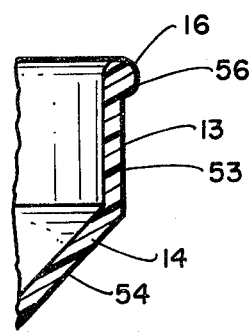
FIG. 9 is a closeup cross section taken along line 9—9 of FIG. 2 and FIG. 6 view of a portion of this invention.

FIG. 9 is provided as a closeup cross sectional view of lip 16 of FIG. 1 and by 56 of FIG. 3 to show how the lip integrates into the upper body portion of the devices of this invention.

Figure 14:
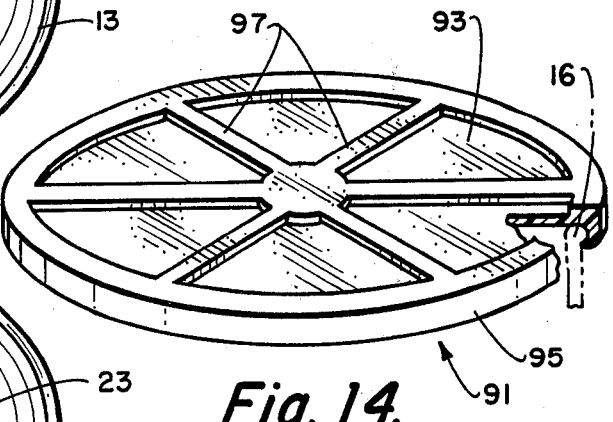
FIG. 14 is a perspective view of an optional lid to be employed with the device of this invention.

FIG. 14 illustrates the lid that is optionally employable to secure the contents of the cups 10 and 50. Lid 91 can be made of such materials as polyethylene or waxed cardstock. Lid 91 includes a generally flat body portion 93 having a series of structures 97 therein for strength. Body section 93 is generally oval and sized slightly larger than the lip 16 or 56 of the two embodiments of the invention. Body 93 includes a concave lip receiving edge 95 that engages the lip 16 or 56 to form a light seal to secure the contents of device 10 or device 50 respectively.

Figure 15:
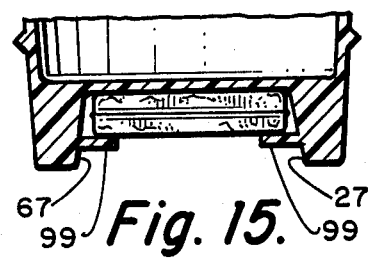
FIG. 15 is a cross section of a variant of a portion of this invention.

FIG. 15 illustrates in perspective an alternate means of mounting the towelette or wiping paper. Here the two ribs 99 depend inwardly from the inner wall 27 of the first embodiment and 67 in the second embodiment. Since the adaptation is applicable to either embodiment a composite view is shown with one leg numbered 27 and the other 67. The towelette 42 is friction fit beneath the bottom wall of the middle portion and the two ribs 99.

Figure 16:
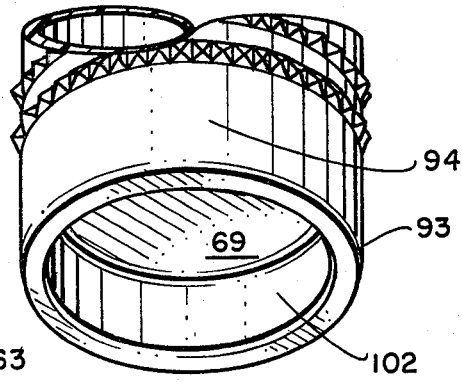
FIG. 16 is a bottom perspective view of a variant of the embodiment of FIG. 7.

FIG. 16 illustrates a variant of the second embodiment. Here the top body portion and the middle portions are the same as shown in FIG. 7. The lower portion is circular in cross section and is uninterrupted. Thus the lower portion 93 comprises a continuous wall 94 extending downwardly from underwall 69. The space 102 inside the wall 94 will have the towelette previously discussed in the first described by adhesing same to the underside of wall 69.

The cups of this invention, especially of the first embodiment, are seen to be mating and thus a great many can be stacked in a small space. We have found that an especially suitable specimen cup can be made from a one piece section of polyethylene that is molded. The oval of the upper section should be sized about $3\frac{1}{2} \times 2\frac{1}{2}$ inches with about 0.5 inches. The elevation of the top section is about 0.5 inches. This has been found to be ideal for men and women. The middle portion is of an elevation of about $\frac{5}{8}$ inches high. The cross section of this portion is about $2\frac{5}{8}$ inches in direction for the oval's longest direction. The bottom portion of the oval configured is about 2 inches in its small direction. The elevation therefore of the lower position which is employed to accumulate the urine is 1 inch high.

Since certain changes may be made in the above apparatus without departing from the scope of the invention herein involved, it is intended that all matter contained in the above description and shown in the accompanying drawings shall be interpreted as illustrative and not in a limiting sense.

I claim:

1. A one piece urine specimen cup, open at the top and comprising an outer wall formed in three portions, the upper two of which are in fluid communication:

the upper portion of which is generally oval in cross section, and which fluidly communicates with a middle portion whose cross section dimensions are smaller than those of the top portion, and which has a bottom wall extending normal to said outerwall, (across a portion of said middle portion), the bottom portion of said cup comprises a pair of spaced apart feet, each having an outer and an inner wall, the inner walls extending upwardly to a generally normal connecting wall that serves as the bottom wall for the middle portion wherein the inner wall of each foot of said cup includes a small inward extending rib spaced down from the bottom wall of said middle portion, and disposed toward the other of said feet thereby forming a resting place for a towelette.

2. The specimen cup of claim 1 further including an outward extending lip at the top edge of the top portion.

3. The specimen cup of claim 1 wherein the middle portion includes a raised area adapted for easy gripability.

4. The specimen cup of claim 1 wherein the top portion is oval and which portion fluidly communicates with a middle portion that is also oval in cross-section.

5. The cup of claim 4 wherein the middle portion's outerwall depends downwardly and inwardly from its locus of connection with the top portion.

6. The cup of claim 1 wherein the middle portion is circular in cross section.

7. The cup of claim 1 wherein the middle portion is of a cylindrical configuration.

8. The specimen cup of claim 1 wherein the spaced apart feet of the lower portion are hollow and thus also in fluid communication with the middle portion.

9. The specimen cup of claim 1 wherein the spaced apart feet are solid and thus are incapable of holding fluid.

10. The cup of claim 1 wherein the feet each have an arcuate outer wall formed as a continuation of and coplanar with the curve of the wall of the middle portion.

11. The cup of claim 10 wherein each foot also includes a bottom horizontal wall for resting on a surface.

12. The cup of claim 1 including an adhesive strip secured to the underside of the bottom of said middle portion.

13. In combination, the urine cup of claim 12 including a body wiping means releasably secured to said adhesive strip.

14. In combination, the urine cup of claim 1 and a towelette disposed in the resting place of the towelette.

* * * * *